(12) United States Patent
Boucher et al.

(10) Patent No.: US 8,062,217 B2
(45) Date of Patent: Nov. 22, 2011

(54) SURGICAL RETRACTOR WITH REMOVABLE BLADES AND METHOD OF USE

(75) Inventors: Wayne Boucher, Manchester, NH (US); James Spitler, Plano, TX (US); Noelle Dye, Charlestown, MA (US)

(73) Assignee: Theken Spine, LLC, Akron, OH (US)

( * ) Notice: Subject to any disclaimer, the term of this patent is extended or adjusted under 35 U.S.C. 154(b) by 624 days.

(21) Appl. No.: 12/021,111

(22) Filed: Jan. 28, 2008

(65) Prior Publication Data
US 2008/0183046 A1 Jul. 31, 2008

Related U.S. Application Data

(60) Provisional application No. 60/886,704, filed on Jan. 26, 2007.

(51) Int. Cl.
*A61B 1/32* (2006.01)
(52) U.S. Cl. .................. 600/215; 600/225; 600/222
(58) Field of Classification Search .................. 600/196, 600/201–246
See application file for complete search history.

(56) References Cited

U.S. PATENT DOCUMENTS

| | | |
|---|---|---|
| 458,457 A | 8/1891 | Hendrickson |
| 643,221 A | 2/1900 | Chapman |
| 708,452 A | 9/1902 | Beist |
| 823,409 A | 6/1906 | Heuston |
| 891,091 A | 6/1908 | Mouthuy |
| 942,523 A | 12/1909 | Sawyer |
| 983,871 A | 2/1911 | Brin |
| 1,275,520 A | 8/1918 | Bell |
| 1,359,164 A | 11/1920 | Giudice |
| 1,412,976 A | 4/1922 | Stanton |
| 1,538,032 A | 5/1925 | Fischer |
| 1,613,141 A | 1/1927 | Stein |
| 1,659,112 A | 2/1928 | Littlejohn |
| 2,109,147 A | 2/1938 | Grosso |
| 2,507,710 A | 5/1950 | Grosso |
| 2,579,849 A | 12/1951 | Newman |
| 2,693,795 A | 11/1954 | Greishaber |
| 3,030,947 A | 4/1962 | Engelbert |
| 3,039,462 A | 6/1962 | Walden et al. |
| 3,054,398 A | 9/1962 | Kobler |
| 3,528,409 A | 9/1970 | Bruder |
| 3,568,665 A | 3/1971 | Lindgren |
| 3,702,606 A | 11/1972 | Barnard |
| 3,716,047 A | 2/1973 | Moore et al. |
| 3,747,591 A | 7/1973 | Golden |
| 3,749,088 A | 7/1973 | Kohlmann |
| 3,807,393 A | 4/1974 | McDonald |
| 3,847,143 A | 11/1974 | Cotey et al. |
| 3,893,454 A | 7/1975 | Hagelin |

(Continued)

*Primary Examiner* — Eduardo C Robert
*Assistant Examiner* — Christina Negrelli
(74) *Attorney, Agent, or Firm* — Middleton Reutlinger; Robert H. Eichenberger; Chad D. Bruggeman

(57) ABSTRACT

Disclosed herein are various embodiments that related to a surgical retractor. In certain embodiments, the retractor may include a blade holder with a single blade tilting mechanism capable of adjusting the angle of a plurality of pivoting blades relative to the blade holder. In certain embodiments, the adjustment occurs from the proximal face or top of the retractor. In other embodiments, blade supports are used to couple the blade holder to a variety of removable blades of different lengths. In certain embodiments, the blades may be a translucent material capable of transmitting light from a proximal portion of the blade to a distal portion. In some embodiments, the distance between the blade holder and the removable blades may be adjusted.

20 Claims, 11 Drawing Sheets

U.S. PATENT DOCUMENTS

| | | |
|---|---|---|
| 4,010,740 A | 3/1977 | Littorin |
| 4,025,053 A | 5/1977 | Stickle, Jr. |
| 4,206,750 A | 6/1980 | Kaivola |
| 4,263,899 A | 4/1981 | Burgin |
| 4,432,351 A | 2/1984 | Hoary |
| 4,496,345 A | 1/1985 | Hasson |
| 4,545,374 A | 10/1985 | Jacobson |
| 4,562,832 A | 1/1986 | Wilder et al. |
| 4,592,344 A | 6/1986 | Scheer |
| 4,597,383 A | 7/1986 | VanDerBel |
| 4,616,635 A | 10/1986 | Caspar et al. |
| 4,627,421 A | 12/1986 | Symbas et al. |
| 4,648,388 A | 3/1987 | Steffee |
| 4,674,501 A | 6/1987 | Greenberg |
| 4,765,311 A | 8/1988 | Kulik et al. |
| 4,852,552 A | 8/1989 | Chaux |
| 4,899,729 A | 2/1990 | Gill et al. |
| 4,905,670 A | 3/1990 | Adair |
| 4,926,849 A | 5/1990 | Downey |
| 4,945,896 A | 8/1990 | Gade |
| 4,957,495 A | 9/1990 | Kluger |
| 5,052,373 A | 10/1991 | Michelson |
| 5,054,906 A | 10/1991 | Lyons, Jr. |
| 5,125,396 A | 6/1992 | Ray |
| 5,139,511 A | 8/1992 | Gill et al. |
| 5,167,662 A | 12/1992 | Hayes et al. |
| 5,183,464 A | 2/1993 | Dubrul et al. |
| 5,195,507 A | 3/1993 | Bilweis |
| 5,234,460 A | 8/1993 | Stouder, Jr. |
| 5,297,538 A | 3/1994 | Daniel |
| 5,312,417 A | 5/1994 | Wilk |
| 5,320,611 A | 6/1994 | Bonutti et al. |
| 5,331,975 A | 7/1994 | Bonutti |
| 5,339,801 A | 8/1994 | Poloyko et al. |
| 5,339,803 A | 8/1994 | Mayzels et al. |
| 5,342,385 A | 8/1994 | Norelli et al. |
| 5,363,841 A | 11/1994 | Coker |
| 5,377,667 A | 1/1995 | Patton et al. |
| 5,395,303 A | 3/1995 | Bonutti et al. |
| 5,423,826 A | 6/1995 | Coates et al. |
| 5,431,658 A | 7/1995 | Moskovich |
| 5,484,437 A | 1/1996 | Michelson |
| 5,496,345 A | 3/1996 | Kieturakis et al. |
| 5,503,617 A | 4/1996 | Jako |
| 5,509,893 A | 4/1996 | Pracas |
| 5,514,076 A | 5/1996 | Ley |
| 5,520,611 A | 5/1996 | Rao et al. |
| 5,540,711 A | 7/1996 | Kieturakis et al. |
| 5,573,517 A | 11/1996 | Bonutti et al. |
| 5,700,263 A | 12/1997 | Schendel |
| 5,704,904 A | 1/1998 | Dunfee |
| 5,704,937 A | 1/1998 | Martin |
| 5,707,359 A | 1/1998 | Bufalini |
| 5,720,746 A | 2/1998 | Soubeiran |
| 5,720,748 A | 2/1998 | Kuslich et al. |
| 5,724,993 A | 3/1998 | Dunfee |
| 5,776,054 A | 7/1998 | Bobra |
| 5,782,753 A | 7/1998 | DeFonzo et al. |
| 5,797,909 A | 8/1998 | Michelson |
| 5,813,978 A | 9/1998 | Jako |
| 5,899,854 A | 5/1999 | Slishman |
| 5,899,901 A | 5/1999 | Middleton |
| 5,902,233 A | 5/1999 | Farley et al. |
| 5,910,155 A | 6/1999 | Ratcliff et al. |
| 5,928,139 A | 7/1999 | Koros et al. |
| 5,931,777 A | 8/1999 | Sava |
| 5,944,658 A | 8/1999 | Koros et al. |
| 5,950,628 A | 9/1999 | Dunfee |
| 5,957,836 A | 9/1999 | Johnson |
| 5,957,902 A | 9/1999 | Teves |
| 5,964,780 A | 10/1999 | Balazs |
| 6,004,337 A | 12/1999 | Kieturakis et al. |
| 6,007,487 A | 12/1999 | Foley et al. |
| 6,017,342 A | 1/2000 | Rinner |
| 6,074,343 A | 6/2000 | Nathanson et al. |
| 6,090,041 A | 7/2000 | Clark et al. |
| 6,099,468 A | 8/2000 | Santilli et al. |
| 6,142,935 A | 11/2000 | Flom et al. |
| 6,171,299 B1 | 1/2001 | Bonutti |
| 6,187,000 B1 | 2/2001 | Davison et al. |
| 6,193,651 B1 | 2/2001 | DeFonzo |
| 6,196,968 B1 | 3/2001 | Rydin et al. |
| 6,214,004 B1 | 4/2001 | Coker |
| 6,224,545 B1 | 5/2001 | Cocchia et al. |
| 6,224,597 B1 | 5/2001 | Coker |
| 6,226,548 B1 | 5/2001 | Foley et al. |
| 6,261,296 B1 | 7/2001 | Aebi et al. |
| 6,340,363 B1 | 1/2002 | Bolger et al. |
| 6,350,236 B1 | 2/2002 | Hipps et al. |
| 6,354,995 B1 | 3/2002 | Hoftman et al. |
| 6,358,266 B1 | 3/2002 | Bonutti |
| 6,364,832 B1 | 4/2002 | Propp |
| 6,379,296 B1 | 4/2002 | Baggett |
| 6,416,470 B2 | 7/2002 | Paolitto et al. |
| 6,428,473 B1 | 8/2002 | Leonard et al. |
| 6,468,206 B1 | 10/2002 | Hipps et al. |
| 6,482,153 B1 | 11/2002 | Hipps et al. |
| 6,488,620 B1 | 12/2002 | Segermark et al. |
| 6,497,654 B1 | 12/2002 | Leonard et al. |
| 6,504,985 B2 | 1/2003 | Parker et al. |
| 6,551,316 B1 | 2/2003 | Rinner et al. |
| 6,530,926 B1 | 3/2003 | Davison |
| 6,554,768 B1 | 4/2003 | Leonard |
| 6,564,078 B1 | 5/2003 | Marino et al. |
| 6,565,574 B2 | 5/2003 | Michelson |
| 6,569,168 B2 | 5/2003 | Lin |
| 6,702,741 B2 | 3/2004 | Rioux et al. |
| 6,712,795 B1 | 3/2004 | Cohen |
| 6,723,044 B2 | 4/2004 | Pulford et al. |
| 6,739,744 B2 | 5/2004 | Williams et al. |
| 6,761,723 B2 | 7/2004 | Buttermann et al. |
| 6,800,084 B2 | 10/2004 | Davison et al. |
| 6,805,666 B2 | 10/2004 | Holland et al. |
| 6,811,558 B2 | 11/2004 | Davison et al. |
| 6,817,978 B2 | 11/2004 | Holland et al. |
| 6,837,851 B1 | 1/2005 | Valentini et al. |
| 6,849,064 B2 | 2/2005 | Hamada |
| 6,869,398 B2 | 3/2005 | Obenchain et al. |
| 6,887,255 B2 | 5/2005 | Shimm |
| 6,929,606 B2 | 8/2005 | Ritland |
| 6,932,764 B2 | 8/2005 | Kashyap |
| 6,945,933 B2 | 9/2005 | Branch et al. |
| 7,014,608 B2 | 3/2006 | Larson et al. |
| 7,056,321 B2 | 6/2006 | Pagliuca et al. |
| 7,079,883 B2 | 7/2006 | Marino et al. |
| 7,108,698 B2 | 9/2006 | Robbins et al. |
| 7,108,705 B2 | 9/2006 | Davison et al. |
| 7,144,368 B2 | 12/2006 | Larson et al. |
| 7,163,510 B2 | 1/2007 | Kahle et al. |
| 7,166,073 B2 | 1/2007 | Ritland |
| 7,179,225 B2 | 2/2007 | Shluzas et al. |
| 7,182,729 B2 | 2/2007 | Abdelgany et al. |
| 7,182,730 B2 | 2/2007 | Fehling |
| 7,189,244 B2 | 3/2007 | Newton et al. |
| 7,195,592 B2 | 3/2007 | Ravikumar et al. |
| 7,207,949 B2 | 4/2007 | Miles et al. |
| 7,210,485 B2 | 5/2007 | Zinkel |
| 7,223,278 B2 | 5/2007 | Davison et al. |
| 7,226,451 B2 | 6/2007 | Shluzas et al. |
| 7,229,408 B2 | 6/2007 | Douglas et al. |
| 7,238,154 B2 | 7/2007 | Ewers et al. |
| 7,238,155 B2 | 7/2007 | Hu et al. |
| 7,261,688 B2 | 8/2007 | Smith et al. |
| 7,261,689 B2 | 8/2007 | Holland et al. |
| 7,306,559 B2 | 12/2007 | Williams |
| 7,371,213 B2 | 5/2008 | Hestad et al. |
| 7,582,058 B1 | 9/2009 | Miles et al. |
| 7,691,057 B2 | 4/2010 | Miles et al. |
| 7,693,562 B2 | 4/2010 | Miles et al. |
| 7,819,801 B2 | 10/2010 | Miles et al. |
| 2003/0191371 A1 | 10/2003 | Smith et al. |
| 2004/0093001 A1 | 5/2004 | Hamada |
| 2004/0176665 A1 | 9/2004 | Branch et al. |
| 2004/0193018 A1 | 9/2004 | Thalgott et al. |
| 2004/0230100 A1 | 11/2004 | Shluzas |
| 2005/0070765 A1 | 3/2005 | Abdelgany et al. |
| 2005/0075540 A1 | 4/2005 | Shluzas et al. |

| | | |
|---|---|---|
| 2005/0096508 A1 | 5/2005 | Valentini et al. |
| 2005/0101985 A1 | 5/2005 | Hamada |
| 2005/0113644 A1 | 5/2005 | Obenchain et al. |
| 2005/0137461 A1 | 6/2005 | Marchek et al. |
| 2005/0148826 A1 | 7/2005 | Paolitto et al. |
| 2005/0159650 A1 | 7/2005 | Raymond et al. |
| 2005/0159651 A1 | 7/2005 | Raymond et al. |
| 2005/0192485 A1 | 9/2005 | Branch et al. |
| 2005/0215862 A1 | 9/2005 | Larson et al. |
| 2005/0234304 A1 | 10/2005 | Dewey et al. |
| 2005/0240209 A1 | 10/2005 | Hamada |
| 2005/0267336 A1 | 12/2005 | Bertolero et al. |
| 2005/0277812 A1 | 12/2005 | Myles |
| 2006/0074278 A1 | 4/2006 | Petit et al. |
| 2006/0074445 A1 | 4/2006 | Gerber et al. |
| 2006/0084981 A1 | 4/2006 | Shluzas |
| 2006/0089536 A1 | 4/2006 | Perez-Cruet et al. |
| 2006/0089652 A1 | 4/2006 | Eckman |
| 2006/0100487 A1 | 5/2006 | Cartier et al. |
| 2006/0106416 A1 | 5/2006 | Raymond et al. |
| 2006/0142642 A1 | 6/2006 | Lins et al. |
| 2006/0142643 A1 | 6/2006 | Parker |
| 2006/0155170 A1 | 7/2006 | Hanson et al. |
| 2006/0167487 A1 | 7/2006 | Hamada |
| 2006/0178693 A1 | 8/2006 | Hamada |
| 2006/0195017 A1 | 8/2006 | Shluzas et al. |
| 2006/0200186 A1 | 9/2006 | Marchek et al. |
| 2006/0200188 A1 | 9/2006 | Nance et al. |
| 2006/0200189 A1 | 9/2006 | Nance et al. |
| 2006/0206008 A1 | 9/2006 | Dalton |
| 2006/0217596 A1 | 9/2006 | Williams |
| 2006/0224044 A1 | 10/2006 | Marchek et al. |
| 2006/0229636 A1 | 10/2006 | Woodburn, Sr. et al. |
| 2006/0235279 A1 | 10/2006 | Hawkes et al. |
| 2006/0241350 A1 | 10/2006 | Nowitzke et al. |
| 2006/0247651 A1 | 11/2006 | Roehm, III et al. |
| 2006/0264968 A1 | 11/2006 | Frey et al. |
| 2006/0271096 A1 | 11/2006 | Hamada |
| 2006/0287584 A1 | 12/2006 | Garcia-Bengochia |
| 2007/0010716 A1 | 1/2007 | Malandain et al. |
| 2007/0021750 A1 | 1/2007 | Shluzas et al. |
| 2007/0027364 A1 | 2/2007 | Schwer |
| 2007/0038032 A1 | 2/2007 | De Canniere et al. |
| 2007/0038033 A1 | 2/2007 | Jones et al. |
| 2007/0038034 A1 | 2/2007 | Sweeney, II |
| 2007/0038216 A1 | 2/2007 | Hamada |
| 2007/0049962 A1 | 3/2007 | Marino et al. |
| 2007/0060793 A1 | 3/2007 | DeGould |
| 2007/0060795 A1 | 3/2007 | Vayser et al. |
| 2007/0073110 A1 | 3/2007 | Larson et al. |
| 2007/0100212 A1 | 5/2007 | Pimenta et al. |
| 2007/0100366 A1 | 5/2007 | Dziedzic et al. |
| 2007/0106123 A1 | 5/2007 | Gorek et al. |
| 2007/0118022 A1 | 5/2007 | Hutton |
| 2007/0118023 A1 | 5/2007 | Smith et al. |
| 2007/0118170 A1 | 5/2007 | Kieturakis et al. |
| 2007/0123753 A1 | 5/2007 | Abdelgany et al. |
| 2007/0129608 A1 | 6/2007 | Sandhu |
| 2007/0156023 A1 | 7/2007 | Frasier et al. |
| 2007/0156024 A1 | 7/2007 | Frasier et al. |
| 2007/0156025 A1 | 7/2007 | Marchek et al. |
| 2007/0156026 A1 | 7/2007 | Frasier et al. |
| 2007/0156027 A1 | 7/2007 | Hu et al. |
| 2007/0158513 A1 | 7/2007 | LeVahn et al. |
| 2007/0161864 A1 | 7/2007 | Sloan |
| 2007/0161865 A1 | 7/2007 | Fakhrai |
| 2007/0179343 A1 | 8/2007 | Shelokov |
| 2007/0198062 A1 | 8/2007 | Miles et al. |
| 2007/0203399 A1 | 8/2007 | Gephart et al. |
| 2007/0208226 A1 | 9/2007 | Grey et al. |
| 2007/0208227 A1 | 9/2007 | Smith et al. |
| 2007/0208228 A1 | 9/2007 | Pavento et al. |
| 2007/0208229 A1 | 9/2007 | Prusmack |
| 2007/0213596 A1 | 9/2007 | Hamada |
| 2007/0225568 A1 | 9/2007 | Colleran |
| 2007/0225571 A1 | 9/2007 | Branch et al. |
| 2007/0238932 A1 | 10/2007 | Jones et al. |
| 2007/0260125 A1 | 11/2007 | Strauss et al. |
| 2007/0276191 A1 | 11/2007 | Selover et al. |
| 2007/0293729 A1 | 12/2007 | Grey et al. |
| 2008/0002426 A1 | 1/2008 | Vayser et al. |
| 2008/0021284 A1 | 1/2008 | Hestad et al. |
| 2008/0058606 A1 | 3/2008 | Miles et al. |
| 2008/0065135 A1 | 3/2008 | Marino et al. |
| 2008/0065144 A1 | 3/2008 | Marino et al. |
| 2008/0086034 A1 | 4/2008 | Schmitz et al. |
| 2008/0086114 A1 | 4/2008 | Schmitz et al. |
| 2008/0132766 A1 | 6/2008 | Dant et al. |
| 2008/0255563 A1 | 10/2008 | Farr et al. |
| 2009/0124860 A1 | 5/2009 | Miles et al. |
| 2009/0259108 A1 | 10/2009 | Miles et al. |
| 2010/0069783 A1 | 3/2010 | Miles et al. |
| 2010/0094093 A1 | 4/2010 | Miles et al. |
| 2010/0105986 A1 | 4/2010 | Miles et al. |
| 2010/0105987 A1 | 4/2010 | Miles et al. |
| 2010/0113884 A1 | 5/2010 | Miles et al. |
| 2010/0137690 A1 | 6/2010 | Miles et al. |
| 2010/0152603 A1 | 6/2010 | Miles et al. |
| 2010/0160738 A1 | 6/2010 | Miles et al. |
| 2010/0174146 A1 | 7/2010 | Miles et al. |
| 2010/0174147 A1 | 7/2010 | Miles et al. |
| 2010/0174148 A1 | 7/2010 | Miles et al. |

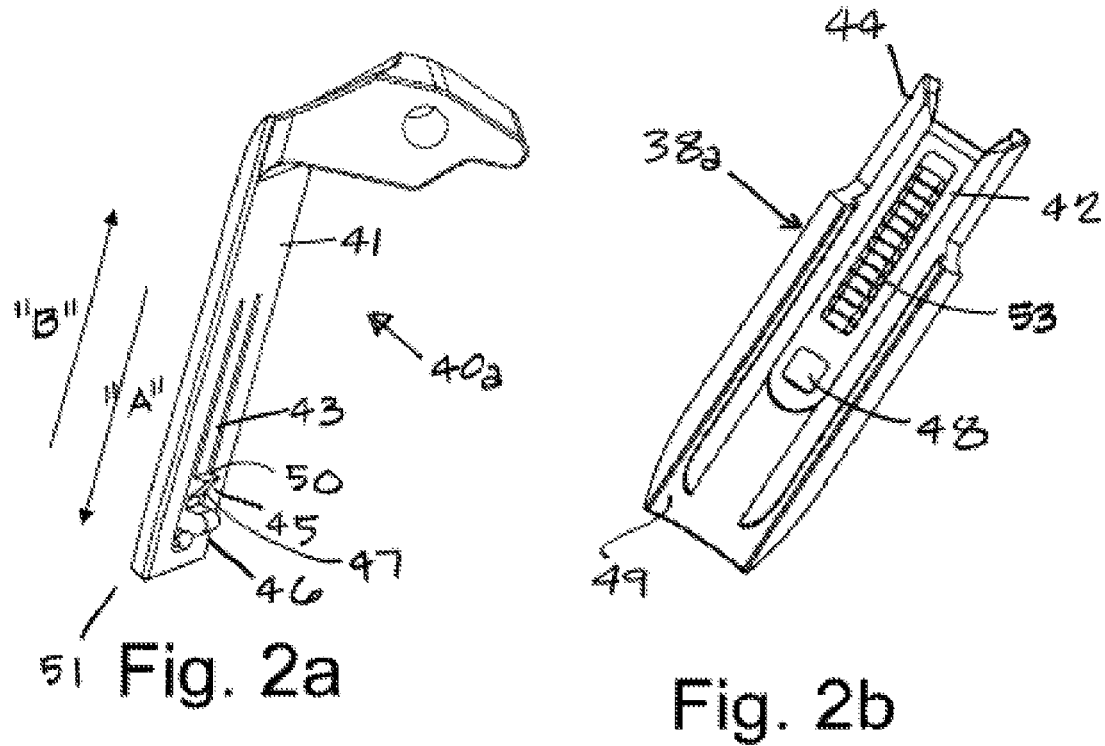
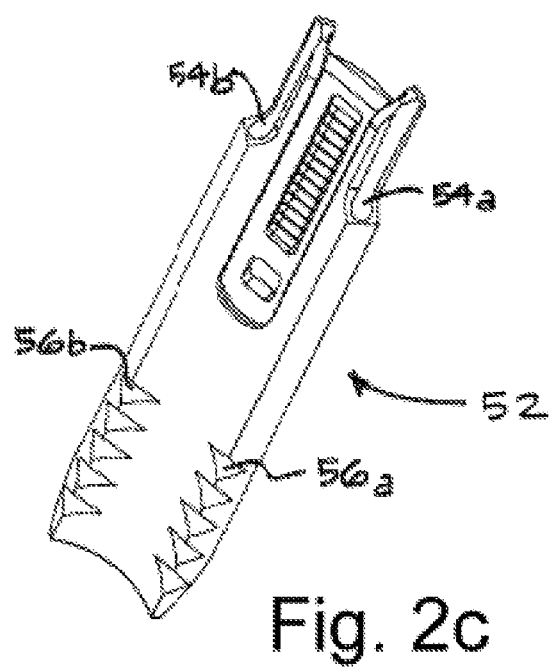

SURGICAL RETRACTOR WITH REMOVABLE BLADES AND METHOD OF USE

PRIORITY CLAIM AND RELATED APPLICATIONS

This application claims priority to U.S. Provisional Patent Application 60/886,704 entitled "SURGICAL RETRACTOR DEVICE AND METHOD OF USE" to Spitler et al. filed Jan. 26, 2007, which is incorporated by reference in its entirety. This application is related to U.S. Utility application Ser. No. 12/021,100, entitled "SURGICAL RETRACTOR WITH ADJUSTABLE BLADES AND METHOD OF USE" to Spitler, et al. filed on the same date as this application, which is also incorporated by reference in its entirety for all purposes.

TECHNICAL FIELD

The present invention relates generally to surgical retractors. More particularly, the invention relates to a surgical retractor for minimally invasive procedures.

BACKGROUND INFORMATION

The human spine provides a vast array of functions, many of which are mechanical in nature. The spine is constructed to allow nerves from the brain to pass to various portions of the middle and lower body. These nerves, typically called the spinal cord, are located in a region within the spine called the spinal canal. Various nerve bundles emerge from the spine at different locations along the lateral length of the spine. In a healthy spine, these nerves are protected from damage and/or undue pressure thereon by the structure of the spine itself.

The spine has a complex curvature made up of a plurality of individual vertebrae (typically twenty-four) separated by intervertebral discs. The intervertebral discs hold the vertebrae together in a flexible manner so as to allow relative movement between the vertebrae from front to back and from side to side. This movement allows the body to bend forward and backward, to bend from side to side, and to rotate about a vertical axis. When the spine is operating properly, the nerves are maintained clear of the hard structure of the spine throughout the available ranges of motion.

Over time or because of accidents or disease, the intervertebral discs may lose height or become cracked, dehydrated, or herniated. The result is that the height of one or more discs may be reduced. The reduction in height can lead to compression of the nerve bundles. Such compression may cause pain and, in some cases, damage to the nerves.

Currently, there are many systems and methods at the disposal of a physician for reducing or eliminating the pain by minimizing the stress on the nerve bundles. In some instances, the existing disc is removed and an artificial disc is substituted therefore. In other instances, two or more vertebrae are fused together to prevent relative movement between the fused discs.

In some procedures, minimally invasive surgical procedures have been developed to fuse or otherwise treat vertebrae. Such procedures can reduce pain, post-operative recovery time, and the destruction of healthy tissue. Minimally invasive surgical procedures are particularly desirable for spinal and neurosurgical applications because of the need for access to locations deep within the body and the possible range of damage to vital intervening tissues.

Generally, it is desirable to access the surgical site using minimally invasive techniques or portals, rather than through a significant incision, to aid in preserving the integrity of the intervening tissues. In such procedures, however, it may be necessary to hold the edges of an incision apart to provide a clear operating field within which the surgeon can operate.

What is needed, therefore, is a tool or retractor adapted to work with minimally invasive procedures that allows the surgeon to have a clear path to the operating field, and a method for using such a tool or retractor.

SUMMARY

Disclosed herein are various embodiments that related to a surgical retractor. In certain embodiments, the retractor may include a blade holder with a single blade tilting mechanism capable of adjusting the angle of a plurality of pivoting blades relative to the blade holder. In certain embodiments, the adjustment occurs from the proximal face or top of the retractor. In other embodiments, blade supports are used to couple the blade holder to a variety of removable blades of different lengths. In certain embodiments, the blades may be a translucent material capable of transmitting light from a proximal portion of the blade to a distal portion. In some embodiments, the distance between the blade holder and the removable blades may be adjusted.

In other embodiments, there is disclosed various methods of retraction during surgery. In some embodiments, the methods include placing a first and second blade assembly of a surgical retractor in an opening in a patient. The length adjustment mechanism is activated to move the first blade assembly away from the second blade assembly and retract tissue. A first set of blades of the first blade assembly is rotated to tilt the first blade assembly and obtain additional tissue retraction with a larger opening located at the distal end of the retractor. In some embodiments, a second set of blades of the second blade assembly is rotated to tilt the second blade assembly and obtain additional tissue retraction with a larger opening located at the distal end of the retractor. In some embodiments, one or more side blades or shims are inserted in the surgical retractor.

In some embodiments described herein, a kit may be provided for a surgical procedure. The kit may include the length adjustment mechanism, at least a pair of blade holders configured to couple to the length adjustment mechanism, at least a pair of blade assemblies configured to couple to the blade holders, and at least one driver configured to activate one or more moving components of the length adjustment mechanism and the blade holders. The kit may also include at least a pair of shims or side blades, a blade adjustor configured to lengthen a portion of a blade assembly, at least one illumination source configured to couple to a blade assembly, and/or a dilator set.

BRIEF DESCRIPTION OF THE DRAWINGS

These and other features, and advantages, will be more clearly understood from the following detailed description taken in conjunction with the accompanying drawings. It is important to note the drawings are not intended to represent the only aspect of the invention.

FIG. 2a is a detailed perspective view of one embodiment of a blade support which may be used in the surgical retractor of FIG. 1a.

FIG. 2b is a detailed perspective view of one embodiment of a blade which may be used in the surgical retractor of FIG. 1a.

FIG. 2c is a detailed perspective view of another embodiment of a blade which may be used in the surgical retractor of FIG. 1a.

FIG. 3 is a partial exploded view of components used in various embodiments of the retractor of FIG. 1a.

FIG. 4 is a partial exploded view of components used in various embodiments of the retractor of FIG. 1a.

FIG. 5 is a detailed perspective view from the top of one embodiment of a component which may be used in the retractor of FIG. 1a.

FIG. 6 is a detailed perspective view from the bottom of one embodiment of a component which may be used in the retractor of FIG. 1a.

FIG. 7 is a partial exploded view from the top of components used in various embodiments of the retractor of FIG. 1a.

FIG. 8 is a partial exploded view from the bottom of components used in various embodiments of the retractor of FIG. 1a.

FIG. 10 is a partial exploded view of components used in various embodiments of the retractor of FIG. 1a.

FIG. 11a is an embodiment of a tray used in a surgical kit incorporating the retractor of FIG. 1a.

FIG. 11b is an embodiment of a tray used in a surgical kit incorporating the retractor of FIG. 1a.

DETAILED DESCRIPTION

Figure 1A:
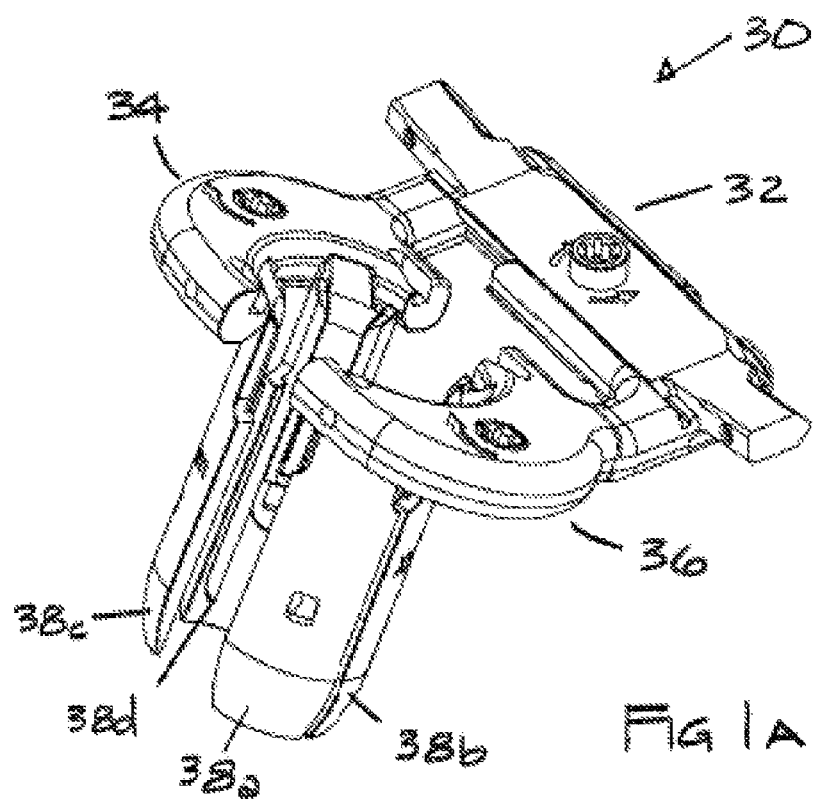
FIG. 1a is an isometric view of one embodiment of a surgical retractor which incorporates one or more aspects of the present invention.

For the purposes of promoting an understanding of the principles of the present inventions, reference will now be made to the embodiments, or examples, illustrated in the drawings and specific language will be used to describe the same. It will nevertheless be understood that no limitation of the scope of the invention is thereby intended. Any alterations and further modifications in the described embodiments, and any further applications of the principles of the inventions as described herein are contemplated as would normally occur to one skilled in the art to which the invention relates.

FIG. 1a depicts an embodiment of a surgical retractor 30. Surgical retractor 30 may include a length adjustment mechanism 32, a first blade holder 34, a second blade holder 36, and a plurality of removable blades 38a-38d. In certain embodiments, the surgical retractor 30 may be used during a surgical procedure to retract tissue of a patient to provide a surgeon access to an operating field. In some embodiments, surgical retractor 30 is used during spinal surgery. However, embodiments of the surgical retractor 30 may also be used during other types of surgical procedures. The surgical retractor 30 may allow for a relatively small opening to be formed in the patient to accommodate needed access to the surgical site during the surgical procedure. When the removable blades 38a-38d are positioned in the opening, the length adjustment mechanism 32 may be used to expand the opening by moving the first and second blade holders 34, 36 away from each other.

Figure 1B:
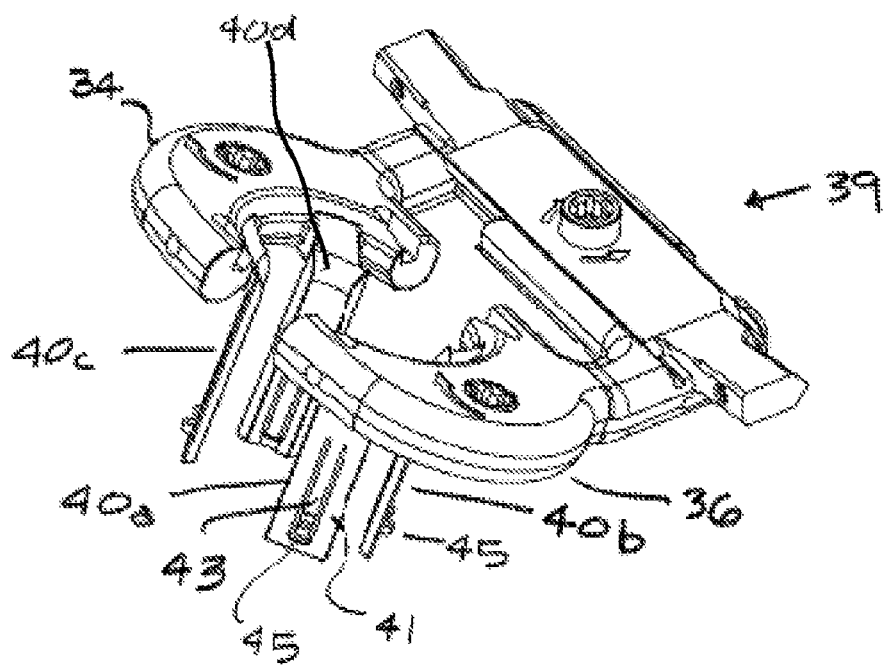
FIG. 1b is the retractor of FIG. 1a with the blades removed.

FIG. 1b illustrates a retractor frame 39, which is the retractor 30 with the removable blades 38a-38d removed. In certain embodiments, a plurality of blade supports 40a-40d are rotatably coupled to the blade holders 34 and 36. The blade supports 40a-40d couple to the removable blades 38a-38d respectively.

Turning now to FIG. 2a, there is a detailed isometric view of a single blade support 40a. In certain embodiments, the blade support may have an exterior structural portion 41 and an interior flexible member 43. In certain embodiments, a pair of protrusions 45 and 46 laterally protrude from a distal end portion of the interior flexible member 43. In the illustrative embodiment, the proximal protrusion 45 is shaped as a V with a sloped distal face 47 and a relatively lateral or flat proximal face 50. In the illustrative embodiment, the distal protrusion 46 may have a semi-circular or bulbous shape.

FIG. 2b illustrates an inside view of one embodiment of a removable blade 38a. As illustrated, removable blade 38a has a longitudinal slot 42 beginning at the proximal end 44. The cross-sectional shape of the longitudinal slot 42 is sized to slidingly receive a distal end portion 51 of the blade support 40a (FIG. 2a). In certain embodiments, there is a row of engagement teeth 53 positioned along a back face of the slot 42. In some embodiments, there is also an adjustment opening 48 through the blade 38a.

In the illustrated embodiment, the space between each of the plurality of teeth 53 is shaped to receive the protrusion 46 of the blade support 40a. When the blade 38a is coupled to the blade support 40a and the blade 38a is traveling in a first direction "A" with respect to the blade support 40a, the sloped distal face 47 of the protrusion 45 allows flexible member 43 to "ride over" the teeth 53. However, the flat face 50 of the protrusion 45 locks the position of the blade 38a in place when the blade 38a is traveling in a direction "B." This adjustability between the teeth 53 and the protrusions 46 and 45 provides a blade length extension mechanism which allows the overall distance of the distal end of the blade 38a to be adjusted with respect to the retractor 30. The adjustment opening 48 is sized to couple to the end of a blade adjustor (not shown). When the blade adjustor forces blade 38a downwards relative to the blade support 40a, the sloped distal face 47 of the protrusion 45 allows the blade to move downwards relative to the blade support.

In certain embodiments, the blade 40a may also have a longitudinal channel or slot 49 for a light mat (not shown). The side edges of the slot 49 maybe angled so a light mat may slide down into slot 49. The angled side edges may keep the light mat coupled to blade 40a. Light mats may be disposable. Certain embodiments, of light mats may be available from LumitexMD, Inc., located in Strongsville, Ohio.

FIG. 2c illustrates another embodiment of a blade 52. In this embodiment, the blade 52 is similar to the blade 40a except that blade 52 may be made from a translucent material capable of transmitting light from a light cable. At the proximal end of the blade 52, there may be one or two slots 54a and 54b for coupling the blade 52 to a light coupler (not shown). In certain embodiments, in order to accommodate the slots 54a and 54b, the blade 52 may be thicker than the blade 40a. In some embodiments, a first end of an optical cable may be coupled to a light source, and a second end of the optical cable may be coupled to the light coupler or to a light mat (as discussed above). The light source may provide light to the light coupler which in turn provides light to the translucent blade 52 to illuminate the operating field established by the surgical retractor. In certain embodiments, the blade 52 may have one or more angled cuts 56a and 56b to specifically direct light to particular regions of the operating field.

In some embodiments, a number of sets of blades of different lengths may be included in a kit provided for a surgical procedure along with the length adjustment mechanism. The blades may be etched or printed with indicia that indicate length. A surgeon may select the desired blade based on length and couple the blade to the retractor.

Figure 3:
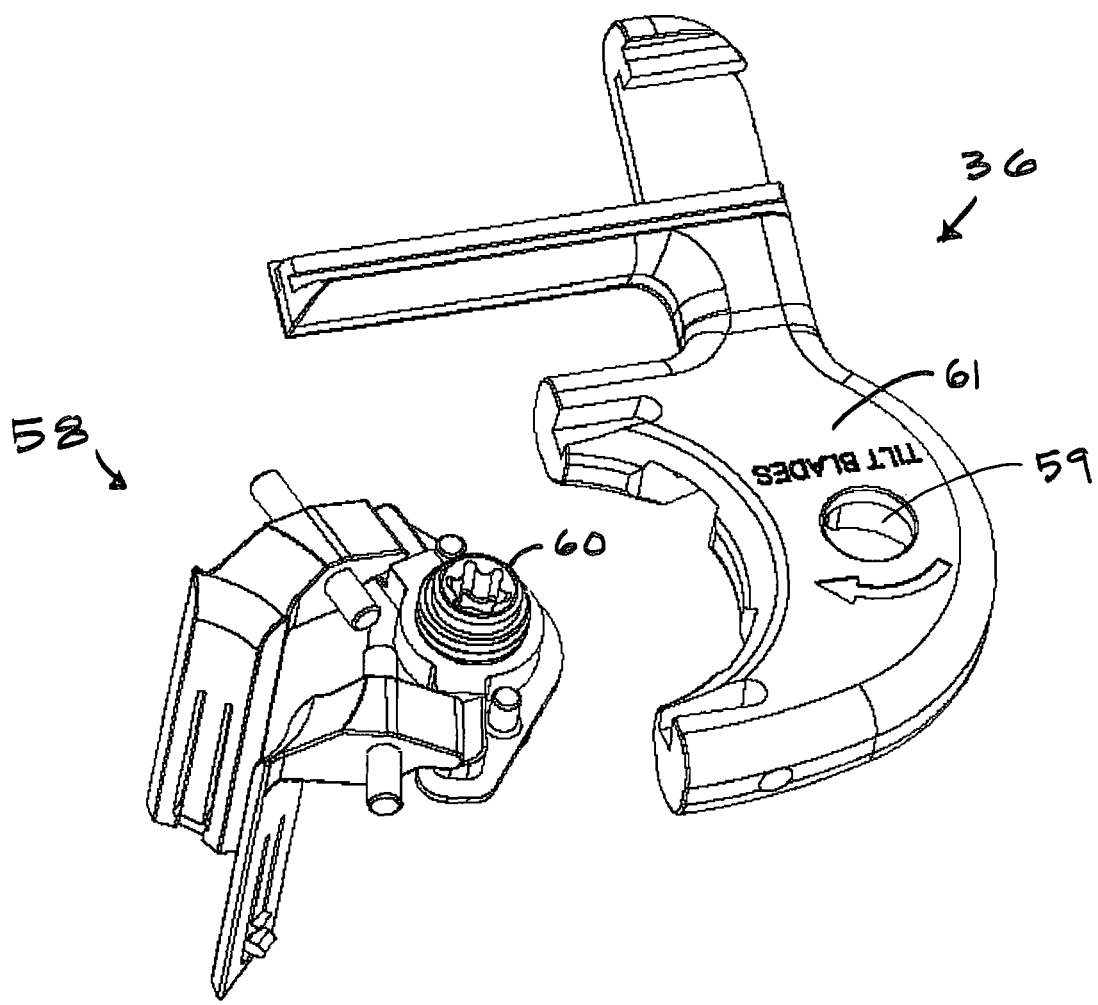

Turning now to FIG. 3, there is illustrated a partial exploded view of a blade angle adjustment mechanism 58 and the second blade holder 36. The angle adjustment mechanism 58 is housed by and works within recesses on the distal face (not shown) of the second blade holder 36. Opening 59 allows access to an angle adjustment activator 60 from the proximal surface 61 of the second blade holder 36.

Figure 4:
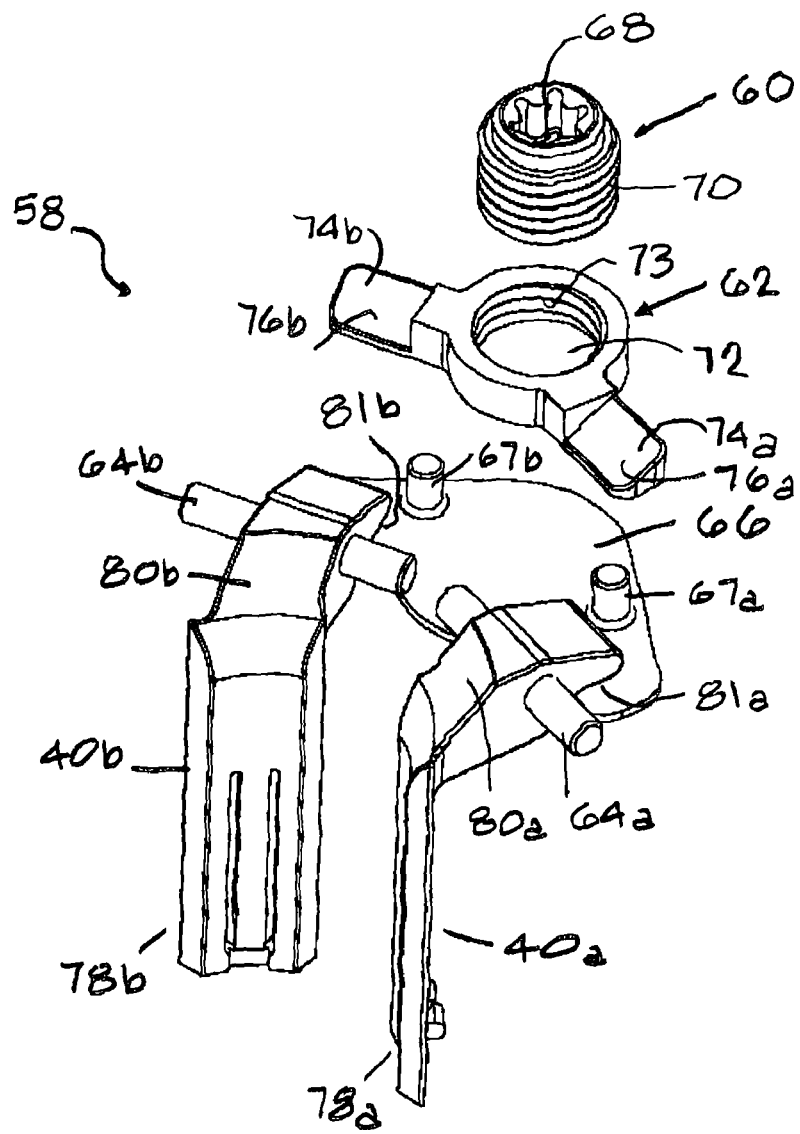

FIG. 4 is a detailed exploded view of just the blade angle adjustment mechanism 58. In certain embodiments, the blade angle adjustment mechanism 58 includes an activator 60, a vertical adjustment member or boss 62, fulcrums or pins 64a and 64b, a back plate 66, connectors 67a and 67b, and the blade supports 40a and 40b. In certain embodiments, the first blade holder 34 (FIG. 1a) contains a similar blade angle adjustment mechanism which may be a mirror image of the blade angle adjustment mechanism 58.

In certain embodiments, the activator 60 may be a threaded member or a screw having a socket 68 sized to engage a corresponding driver (not shown). External threads 70 on the activator 60 may engage internal threads 73 in a center bore 72 of the vertical adjustment member 62. In certain embodiments, the vertical adjustment member may include cam wings 74a and 74b. Each cam wing 74a-74b may include sloped surfaces 76a and 76b, respectively.

In certain embodiments, the blade support 40a includes a leg portion 78a and a yoke portion 80a. The yoke portion 80a has a bore to couple to the fulcrum or pin 64a. In certain embodiments, the yoke portion 80a has a sloped interior surface 81a to allow easier access to the surgical site. The ends of the pin 64a fit within circular openings in the second blade holder 36 (not shown) which support the pin and allows the pin to rotate relative to the second blade holder.

Similarly, the blade support 40b includes a leg portion 78b and a yoke portion 80b which may be coupled to the pin 64b. The pin 64b is also supported by circular openings in the second blade holder 36.

When the activator 60 is rotated with a driver (not shown), the rotation of the activator causes the vertical adjustment member 62 to move longitudinally with respect to the activator 60. Thus, rotating the activator 60 causes the cam wings 74a and 74b to also move vertically. When the cam wings 74a and 74b move up, the sloped surfaces 76a and 76b engage corresponding sloped surfaces 81a and 81b on the respective yoke portions 80a and 80b. This upward force on the sloped surfaces 81a and 81b causes the respective yoke portions 80a and 80b to pivot about the pins 64a and 64b, which in turn rotates the leg portions 78a and 78b in an outward direction.

Thus, in some embodiments, rotation of activator 60 causes a range of rotation from an initial position where the blade supports are substantially perpendicular to a central axis of second blade holder 36 up to an angle of about 30°. In other embodiments, a smaller or greater range of rotation of the blade assembly may be achieved by the cam wings. Thus, once the retractor is in the surgical incision in the patient, the distal end of removable blades 38a-38d spread by rotating or tilting the blade supports. This rotation increases the area of retracted tissue so that the area is larger at the distal end of the blades of the surgical retractor than near blade holders 34, 36. Providing a larger area at the distal end of the surgical retractor may advantageously provide better visualization of the operating field.

Figure 5:
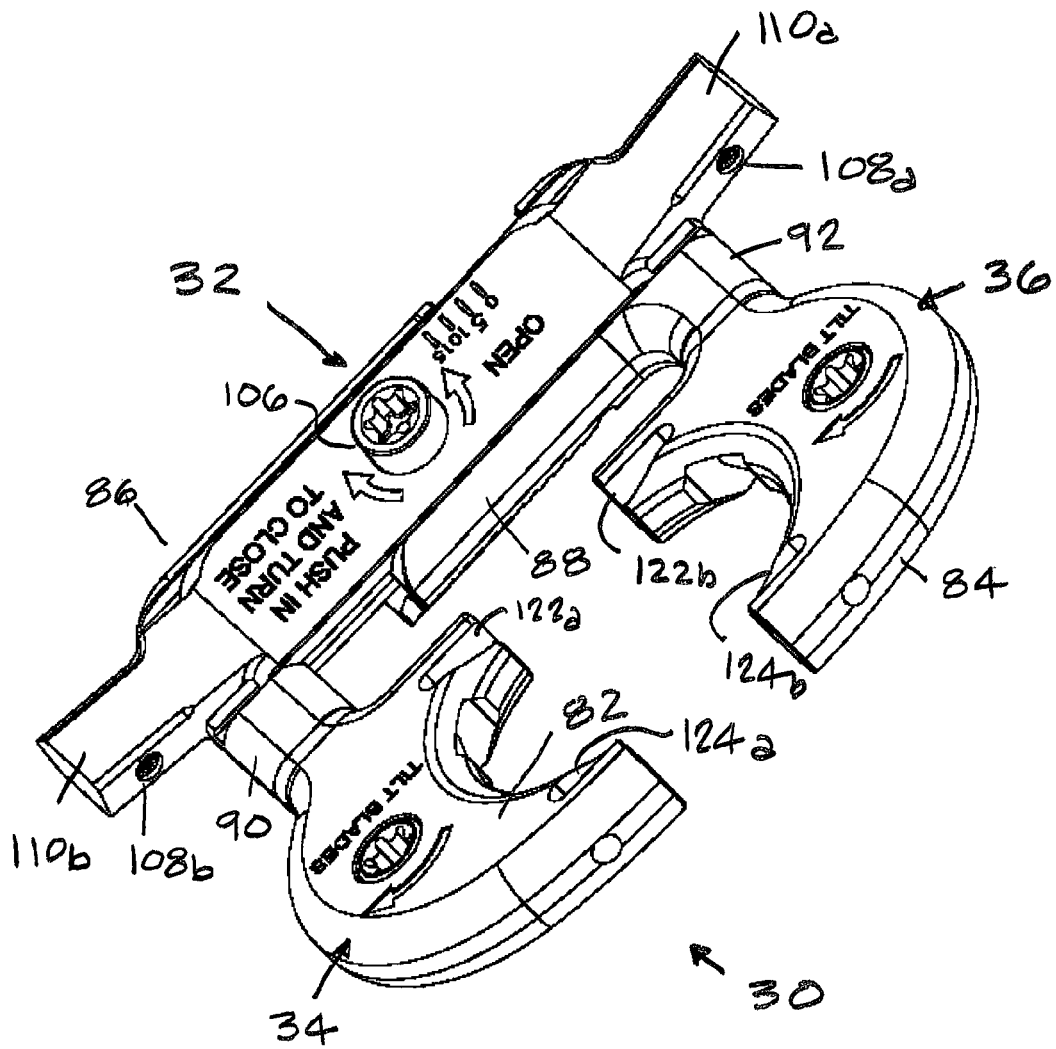
Figure 6:
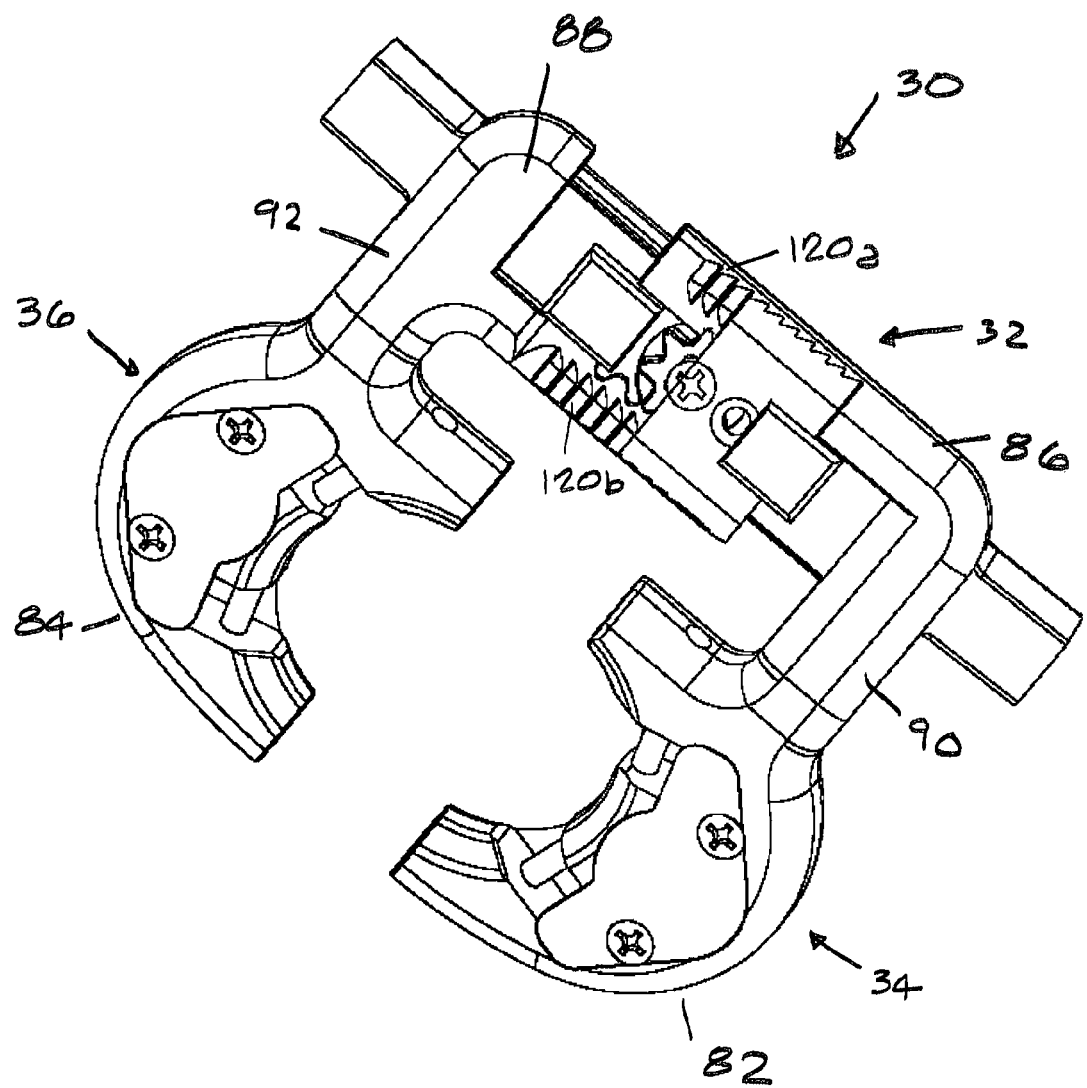
Figure 7:
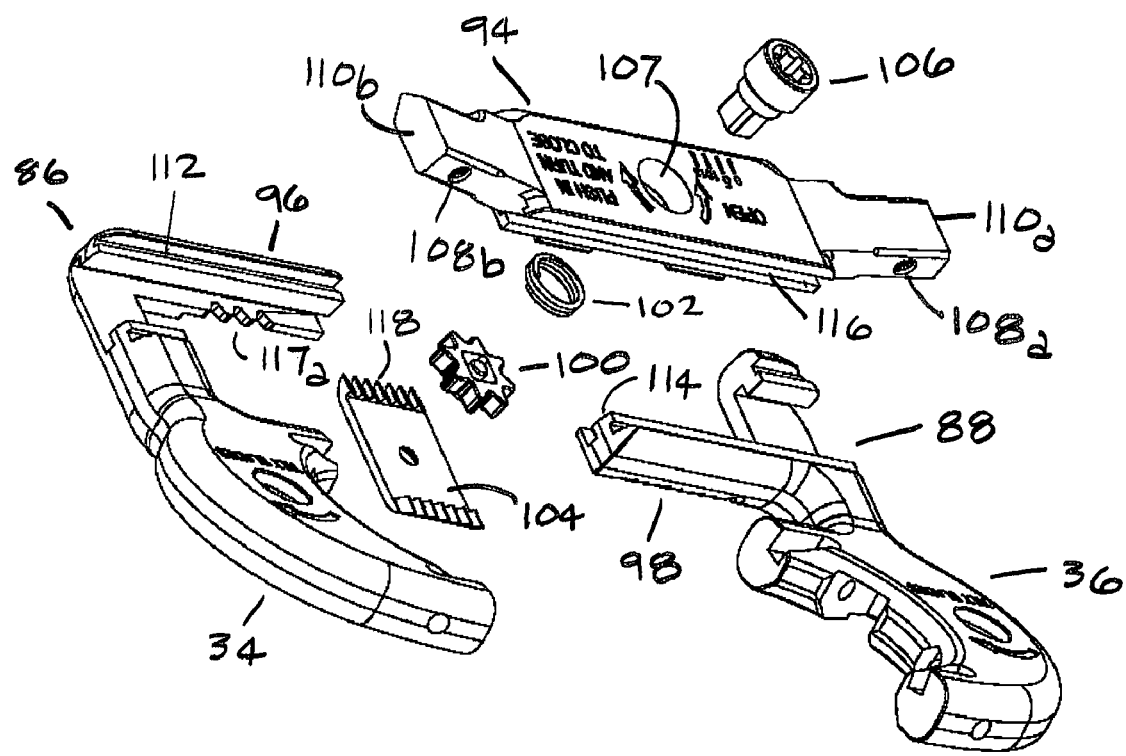
Figure 8:
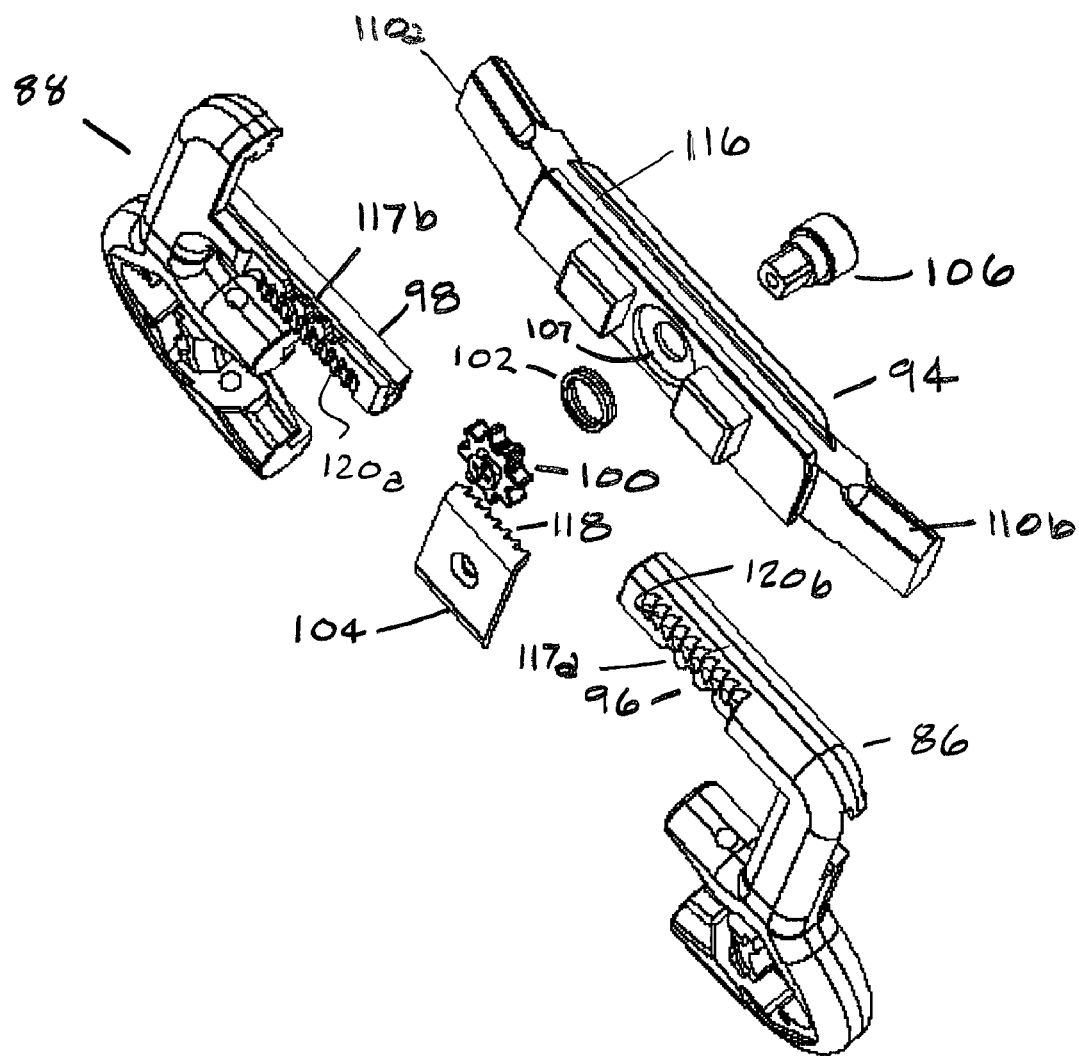

FIG. 5 is a top perspective view of the retractor 30 and FIG. 6 is a bottom perspective view of the retractor 30. In these figures and in FIGS. 7 and 8, the blades and blade supports have been removed for clarity. As illustrated, the retractor 30 comprises the first blade holder 34, the second blade holder 36, and the length adjustment mechanism 32. In some embodiments, each of the blade holders 34, 36 have blade holding portions 82 and 84 and length adjustment portions 86 and 88. As illustrated, each of the respective length adjustment portions 86 and 88 are laterally separated from the blade holding portions 82 and 84 by arms 90 and 92.

In certain embodiments, the length adjustment mechanism 32 inhibits undesired movement of first blade holder 34 relative to second blade holder 36 so that retracted tissue does not result in the first blade holder being forced towards the second blade holder with a resulting decrease in the size of the opening. In some embodiments, the length adjustment mechanism 32 of surgical retractor 30 may allow for relative movement of first blade holder 34 towards or away from second blade holder 36. In some embodiments, first blade holder 34 moves the same distance but in an opposite direction relative to second blade holder 36. Movement of first blade holder 34 relative to the second blade holder 36 the same distance but in an opposite direction allows for equal expansion of blades assemblies 38 relative to a midline between the blade holders.

In some embodiments, the length adjustment mechanism 32 is a rack and pinion type of mechanism as illustrated in FIG. 6. For purposes of this discussion, also refer to FIG. 7, which is an exploded view of the length adjustment mechanism 32 from the top and FIG. 8 which is an exploded view from the bottom.

In certain embodiments, the length adjustment mechanism 32 may include a bar 94, a first rack 96, a second rack 98, a pinion 100, a biasing member 102, a stop 104 and an activator 106. In the illustrated embodiment, the first rack 96 and the second rack 98 are integral with the first blade holder 34 and the second blade holder 36. In other embodiments, the racks 96 and 98 could be portions of a separate length adjustment mechanism as illustrated in U.S. Utility application Ser. No. 12/021,100, entitled "SURGICAL RETRACTOR WITH ADJUSTABLE BLADES AND METHOD OF USE" to Spitler, et al. filed on the same date as this application.

In some embodiments, the bar 94 may include recesses 108a and 108b and couplers 110a and 110b that allow the surgical retractor 30 to be coupled to a surgical table to stabilize and fix the position of the surgical retractor relative to the patient. In other embodiments, the bar 94 or other portions of the surgical retractor may include connection features that allow the surgical retractor to be coupled to the surgical table such as, but not limited to recesses, threaded openings, protrusions, grooves, slots, and/or quick release mechanisms.

In the illustrated embodiment, the first rack 96 of the first blade holder 34 and the second rack 98 of the second blade holder 36 have longitudinal tongue and groove members 112 and 114 which engages corresponding grooves 116 on the bar 94 to allow the racks to slide along the bar 94. In certain embodiments, the first rack 96 and second rack 98 may include lateral gear teeth 117a and 117b, respectively that engage gear teeth of pinion 100.

Pushing the activator 106 downwards disengages the stop 104 and allows the pinion 100 to engage the respective teeth 117a and 117b of the racks 96 and 98. Thus, rotating the pinion moves the first rack 96 towards or away from the second rack 98. In certain embodiments, indicia placed on, printed on or etched in the bar 94 and/or the racks 96 and 98 may indicate direction of travel of first rack and/or second rack when the pinion 100 is rotated in a clockwise direction or counterclockwise direction. In other embodiments, the length adjustment mechanism 32 may include a threaded shaft and a wheel or other type of adjustment mechanism that allows for movement of the first blade holder of the surgical retractor relative to the second blade holder of the surgical retractor.

When the serrations 118 of stop 104 are positioned in the corresponding serrations 120a-120b of the first rack 96 and the second rack 98 respectively, movement of the first rack relative to the second rack is inhibited. Thus, the stop 104 inhibits undesired movement of the first rack 96 relative to the second rack 98 so that undesired movement of the blade holders coupled to the length adjustment mechanism is inhibited. In turn, the stop 104 may inhibit force applied to the blade assemblies by retracted tissue from reducing the size of the opening established by the surgical retractor.

In certain embodiments the activator 106 may be connected to the stop 104 by using a connector such as a screw (not shown) at the distal end of the activator. The opening 107 positioned within the bar 94 may be sized to allow the activator 106 to travel longitudinally with respect to the longitudinal axis of the opening. The biasing member 102, such as a helical spring may keep the activator 106 biased in a first position which extends laterally from the bar 94 as illustrated in FIG. 5. Therefore, pushing the activator 106 to a second position with a driver (not shown) compresses the spring 102 and pushes the stop 104 down to disengage serrations 118 of the stop 104 from the mating serrations 120a and 120b on the bottom faces of the first rack 96 and the second rack 98, respectively. When the serrations 120a and 120a are disengaged, the first rack 96 is free to travel with respect to the second rack 98 when the pinion 100 is rotated by engaging the activator 106. In other embodiments, the activator 106 could be shaped so that when pressed the activator 106 to a third position, both the pinion 100 and the serrations of the stop 104 are disengaged causes the blade holders 34 and 36 to quickly release.

Thus, in some embodiments, once the retractor is in the surgical incision in the patient, the distance between the blade holders 34 and 36 may be increased by using the length adjustment mechanism. Adjusting the distance between the blade holders also increases the length of the surgical area. Providing a larger area at the distal end of the surgical retractor may advantageously provide better visualization of the operating field.

Figure 9:
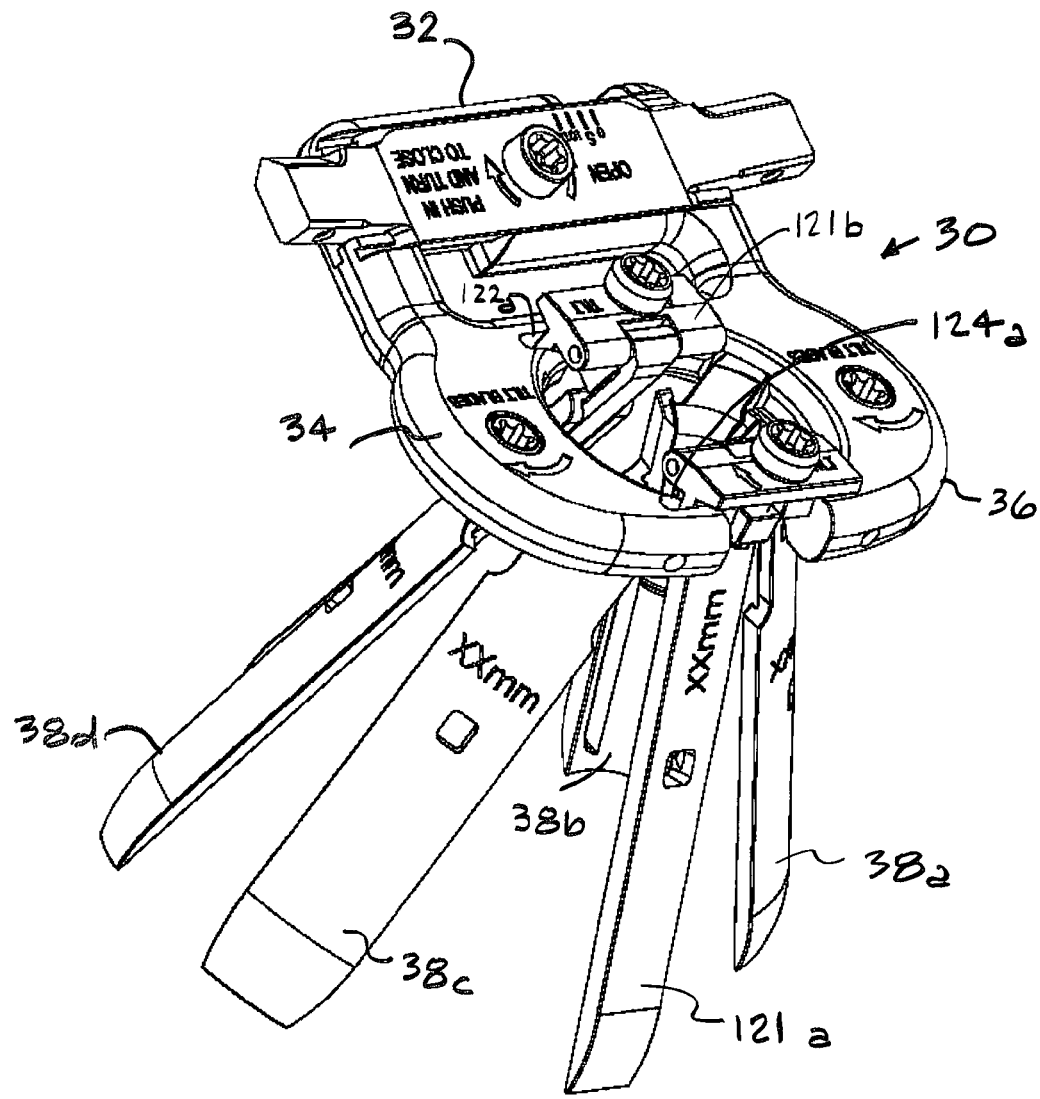
FIG. 9 is a perspective view of one embodiment of a surgical retractor of FIG. 1a which incorporates one or more aspects of the present invention.

When the distance between the pair of blades is increased, the possibility for lateral incursion of tissue between the blades increases. Turning now to FIG. 9, there is depicted an embodiment of surgical retractor 30 using side blades or shim assemblies 121a and 121b to retain any lateral tissue. As illustrated, the shim assemblies 121a and 121b may be positioned between the blade holders 34 and 36. In FIG. 9, the length adjustment mechanism 32 has been used to separate the blade holders 34 and 36 to a sufficient distance to allow portions of the shim assemblies 121a and 121b to be inserted into corresponding shim recesses on the top face of blade holders 34, 36. In FIG. 9, a portion of shim recesses 122 and 124 are visible in blade holder 34. A better view of the shim recesses 122a-122b and 124a-124b, however, may be found in FIG. 5 which illustrates the blade holders 34 and 36 with the shim assemblies and blades removed.

Turning back to FIG. 9, note that blades 38a-38d as illustrated are in an expanded or rotated position. In other words, as discussed previously, the angle adjustment mechanisms of the blade holders 34 and 36 have been used to rotate the blade supports which in turn rotate the blades 38a-38d. The shim assemblies 121a and 121b are also in a rotated position. In contrast, FIG. 1 depicts the surgical retractor 30 where the blades 38a-38d are in an initial or un-rotated position.

Figure 10:
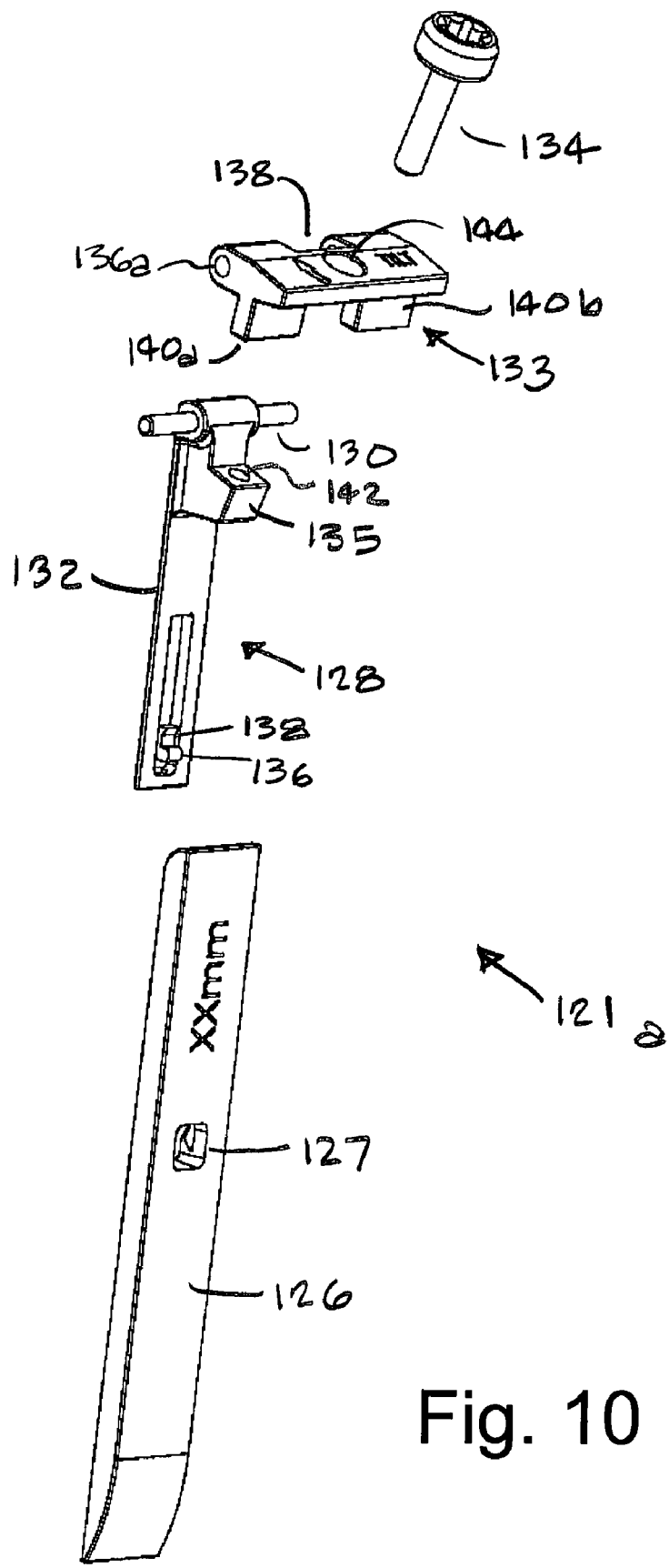

FIG. 10 depicts an exploded view of an embodiment of the shim assembly 121a. In some embodiments, the shim assembly 121a may be positioned in the side blade recesses 122a-122b or 124a-124b in the respective blade holders 34 and 36 (FIG. 5) when the blade holders are separated by a predetermined distance, for instance, 30 mm. In other embodiments, the size of the side blades may be adjusted to accommodate other minimum separation distances of the blades holders.

The shim assembly 121a may include blade or shim 126, a shim support 128, a fulcrum or pin 130, a mount 133, and an activator 134. In certain embodiments, the shim 126 may have a longitudinal slot (not shown) for receiving the shim support 128. The shim support 128 may have a distal or leg portion 132 and a lever portion 135. In certain embodiments, the leg portion 132 may have protrusions 136 and 138. The protrusions 136 and 138 may engage a plurality of teeth on the back face of the longitudinal slot (not shown) of the shim 126. The protrusions 136 and 138 may engage the teeth and be adjusted in a manner similar to the protrusions 45 and 46 discussed in reference to FIGS. 2a and 2b. Thus, the position of the shim 126 may be adjusted with respect to the shim support 128 in a manner similar to the way the blades may be adjusted with respect to the blade supports as discussed above. Consequently, the shim 126 includes a through opening 127 for engaging a blade adjuster (not shown).

In certain embodiments, the pin 130 may couple the lever portion 135 of the shim support 128 to the mount 133 and allow the shim support to rotate relative to the mount about the longitudinal axis of the pin. The mount 133 may have circular openings 136a and 136b for receiving and supporting the pin 130 (only opening 136a is visible in FIG. 10). A side notch 138 may be sized to receive a portion of the shim support 128 so that the shim support can rotate when the pin 130 is coupled to both the shim support and the mount 133. The mount 133 may have bottom projections 140a and 140b which are sized to be positioned within the shim recesses 122a-122b or 124a-124a of the respective blade holder (FIG. 5). The activator 134 may be coupled to mount 133 and to the lever portion 135 of the shim holder 128. The activator 134 may include male threading that complements female threading in an opening 142 of lever portion 135. The diameter of the activator 134 may be sized to freely pass through a bore 144 positioned within the mount 133.

When the bottom projections 140a and 140b are positioned in the shim recesses of the respective blade holders, rotation of the activator 134 in a clockwise direction may draw the lever portion 135 of the shim support 128 towards the mount 133. This movement will cause the leg portion 132 of the shim support 128 to rotate about the pin 130 so that the distal end of shim 126 moves outwards from the blade holders.

In certain embodiments, an indicator may be etched, decaled, or printing on the face of the mount 133 to indicate a direction of rotation of the activator 134 to tilt the shim. In some embodiments, rotation of the activator 134 allows the shim to tilt up to about 15° from vertical. In other embodiments, rotation of the activator 134 may allow the shim 126 to rotate in a range that is greater or less than 15° from vertical.

In some embodiments, the blades may be insertable and removable from the blade supports before a surgical procedure. A number of blade assembly pairs of various lengths may be included in a kit provided for a surgical procedure along with various pairs of blade holders and the length adjustment mechanism. Having insertable and removable blade assemblies may significantly reduce the size and weight of the kit provided for the surgical procedure since only relatively few pairs of blade holders are needed and not a pair of blade holders for each pair of blade lengths. Also, the length adjustment mechanism and the blade supports may be formed as a single non-separable unit when insertable and removable blade assemblies are used. Blade assemblies may be positioned in or removed from the blade holders and the length adjustment mechanism combination as the situation warrants.

Thus, the surgical retractor 30 may be provided as part of a surgical kit. The kit may include one or more cases that hold accessories, instruments, and the components of the surgical retractor. The cases may have a plurality of openings. In certain embodiments, the entire case may be placed in a sterilizer to sterilize all of the contents within the case. Some of the contents in the case may be pre-sterilized and placed in bags that are put into the case. Accessories included in the case may include MediFlex Arm and Table Mount (Mediflex Surgical Products, Islandia, N.Y.), a table adaptor, light cables and adaptors, disposable light mats, and trays.

Figure 11A:
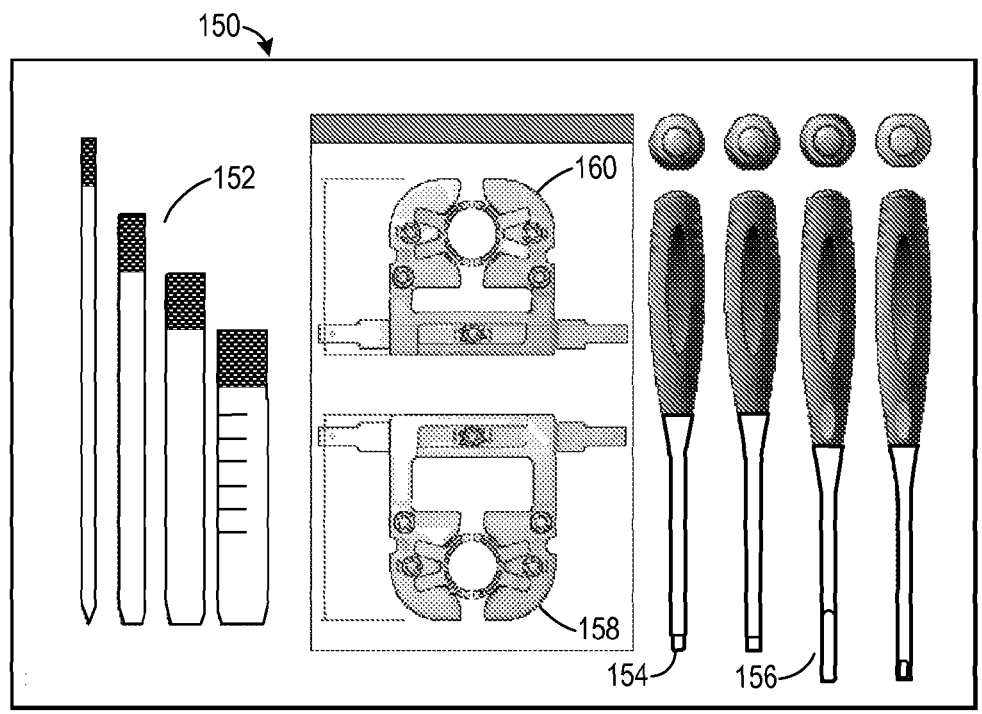
Figure 11B:
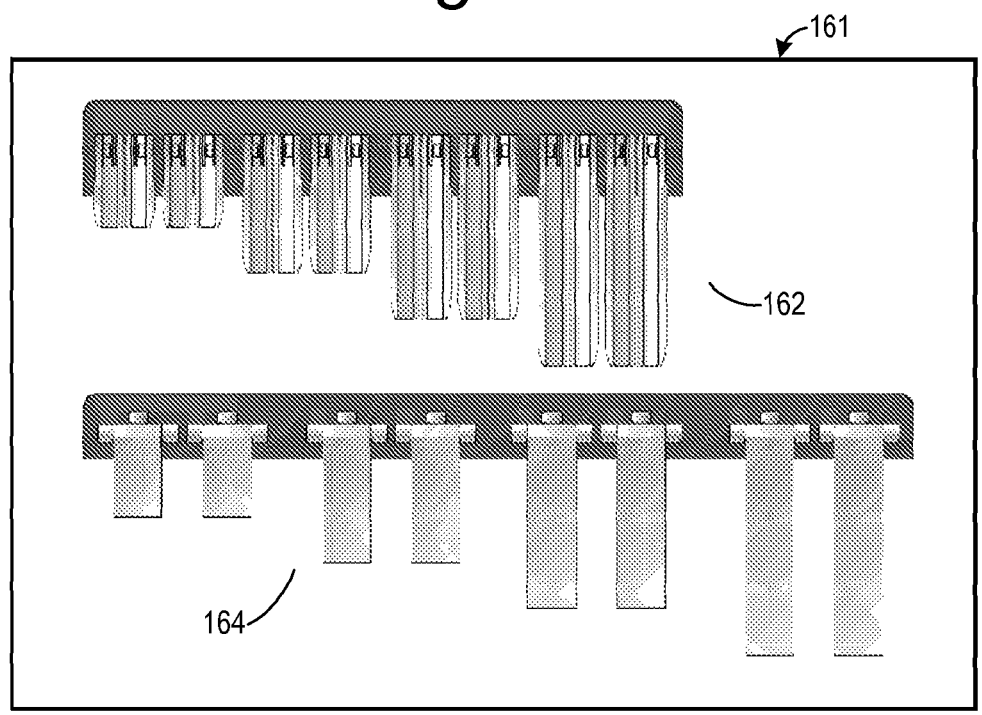

Two possible tray embodiments of a kit are illustrated in FIGS. 11a and 11b. Referring to FIG. 11a, the instruments included in the tray 150 may include a dilator set 152, a pair of drivers 154, and a pair of blade adjusters 156, and one or more lateral retractor frames 158 and 160. In certain embodiments, the dilator set 152 may be used to expand the initial incision made in the patient. The pair of drivers 154 may turn the various activators of the angle adjustment mechanism, the length adjustment mechanism and the shim assembly activators. The pair of drivers 154 may be included so that the same task can be simultaneously performed on the first and second blade holders of the surgical retractor. Handles of the drivers may be ratcheting or non-ratcheting handles. The retraction device may be used to draw tissue out of the way when side blades are installed in the surgical retractor. The pair of blade adjusters 156 may be used to couple with various openings in the blades or shims so that the distance between the blades and blade supports may be adjusted—effectively lengthening the blade lengths.

In certain embodiments, there may also be one or more retractor frames 158 and 160. A "retractor frame" may be defined to be a retractor without the blades or shims (as illustrated in FIG. 1B). A number of different retractor frames may be provided where each retractor frame has different length retractor arms (e.g. arms 90 and 92 of FIG. 5). Different length retractor arms will vary the distance between the blade holders and the length adjustment mechanisms, which allow for various sized openings between the blade holders and the length adjustment mechanisms. Additionally the angle between the blade holders and length adjustment mechanisms could vary between the retractor frames. Surgeons may have different preferences on the size of the openings or the angle. So, providing a plurality of retractor frames allow the surgeon to determine the best configuration for the surgery.

Turning now to FIG. 1b, there is an embodiment of a second tray 161 of the kit containing a plurality of removable blade assemblies 162 of different lengths and a plurality of shim assemblies 164 of different lengths. In each assembly of removable blades, there may be four removable blades of the same length. In each assembly of shims, there may be two shims of the same length. For instance, in transforaminal or posterior lumbar approaches, the blade assemblies included in the kit may have lengths of 40 mm, 50 mm, 60 mm, 70 mm, and 80 mm. For extreme lateral lumbar approaches (e.g., an XLIF procedure), the blade assemblies included in the kit may have lengths of 90 mm, 100 mm, 110 mm, 120 mm, and 130 mm. Other sizes and quantities may also be included in the kit.

Various surgical accessories in the retractor kit may be prepared before the surgery. For instance, a flexible arm may be attached to the surgery table or to a table mount. If light mats or translucent blades are to be used, the light source may be prepared and optical cables inserted. The length adjustment mechanism may be adjusted so that the blade holders are close together. A retractor frame may be selected and coupled to the flexible arm or a table mount.

When the surgical procedure begins, an incision may be formed in the patient. The incision may be expanded using the set of dilators 152. A retractor frame may be selected and turned upside down. The removable blades of a particular length may then be selected and coupled to the blade supports of the retractor frame. When the blades of the surgical retractor are in an initial close together position, the blades assemblies may closely match the outside diameter of the largest dilator so that the blade assemblies may be guided into the patient along the outside surface of the largest dilator. The surgeon or operating theater personnel may then grasp the blade holders and position the blade assemblies in the incision.

Correct positioning may require checking the retractor angulation with respect to the patient. Furthermore, positioning of the retractor and flexible arm may need to be checked for proper optical and radiographic visualization relative to the patient's anatomy. The table mount and/or flexible arm may then be locked in position and the blades may be seated against the bony elements of the anatomy. The drivers may then be removed and light mats are seated or optic cables are coupled to optical couplings in the blades.

The retractor may then be longitudinally expanded. A driver may be used to turn the activator which drives pinion of the length adjustment mechanism to move the blade holders away from each other and retract tissue.

During some procedures, the driver or drivers may be used to rotate the activators for the angle adjustment mechanisms of the respective blade holders. Rotating the activator caused the cam surfaces to lift and rotate the yoke portions of the blade supports, which tilts the blades of the respective blade holder to achieve additional tissue retraction. Tilting the blades moves the distal ends of the blades of the blade assembly outwards creating a larger opening near a distal end of the blade assembly. After the blades are tilted, the blades can be extended with respect to the blade holder with a blade adjustor.

When the blade holders are at desired distance apart, bottom projections of the shims may be positioned in the shim recesses, if needed. In some embodiments, the drivers or a driver may be used to rotate an activator of a shim. Rotating an activator of a shim may tilt the shim so that the distal end of the side blade moves outwards.

After the surgical retractor is positioned and set up, the surgical procedure may be performed. After the surgical procedure, a driver may be used to rotate the pinion so that the blade holders and blade assemblies are drawn close together. The surgical retractor may then be removed from the patient.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

It is understood that terms such as "side", "top", "bottom", "front", "back", "proximal", and "distal" are relative and may be interchangeable depending on the perspective from which the device of the present disclosure is being viewed. Accordingly, such terms are used for purposes of illustrating and describing various embodiments of the present disclosure and are not intended to be limiting. When the term "proximal" is used it refers to the portion of a component that is closer to the user when the embodiment is used in its intended manner. Similarly, when the term "distal" is used, the term refers to the portion of a component that is farther from the user when the embodiment is used in its intended manner.

The abstract of the disclosure is provided for the sole reason of complying with the rules requiring an abstract, which will allow a searcher to quickly ascertain the subject matter of the technical disclosure of any patent issued from this disclosure. It is submitted with the understanding that it will not be used to interpret or limit the scope or meaning of the claims.

Any advantages and benefits described may not apply to all embodiments of the invention. When the word "means" is recited in a claim element, Applicant intends for the claim element to fall under 35 USC 112, paragraph 6. Often a label of one or more words precedes the word "means". The word or words preceding the word "means" is a label intended to ease referencing of claims elements and is not intended to convey a structural limitation. Such means-plus-function claims are intended to cover not only the structures described herein for performing the function and their structural equivalents, but also equivalent structures. For example, although a nail and a screw have different structures, they are equivalent structures since they both perform the function of fastening. Claims that do not use the word means are not intended to fall under 35 USC 112, paragraph 6.

The foregoing description of the embodiments of the invention has been presented for the purposes of illustration and description. It is not intended to be exhaustive or to limit the invention to the precise form disclosed. Many combinations, modifications and variations are possible in light of the above teaching. Undescribed embodiments which have interchanged components are still within the scope of the present invention. It is intended that the scope of the invention be limited not by this detailed description, but rather by the claims appended hereto.

What is claimed is:

1. A surgical retractor, comprising:
a first blade holder,
a second blade holder,
the length adjustment mechanism slidingly coupled to the first blade holder and the second blade holder, the length adjustment mechanism configured to move the first blade holder relative to the second blade holder;
a first blade angle adjustment mechanism coupled to the first blade holder and a first and third blade, the first blade angle adjustment mechanism including:
a first activator,
a first boss coupled to the first activator such that when the first activator is activated, the first boss moves in a longitudinal direction with respect to the first activator,
a first fulcrum coupled to the first blade holder,
a first yoke pivotedly coupled to the first fulcrum having a driving lever portion coupled to the boss and a follower lever portion,
a first leg portion coupled to the follower lever portion,
wherein the first blade is coupled to the first leg portion such that when the first boss moves in the longitudinal direction with respect to the activator, the first yoke pivots about the first fulcrum causing the first blade to rotate,
a third fulcrum coupled to the first blade holder,
a third yoke pivotedly coupled to the third fulcrum having a driving lever portion coupled to the boss and a follower lever portion,
a third leg portion coupled to the follower lever portion,
wherein the third blade is coupled to the third leg portion such that when the first boss moves in the longitudinal direction with respect to the activator, the third yoke pivots about the third fulcrum causing the third blade to rotate, and
a second blade angle adjustment mechanism coupled to the second blade holder and a second and fourth blade, the second blade angle adjustment mechanism including:
a second activator,
a second boss coupled to the second activator such that when the second activator is activated, the second boss moves in a longitudinal direction with respect to the second activator,
a second fulcrum coupled to the second blade holder,
a second yoke pivotedly coupled to the second fulcrum having a driving lever portion coupled to the boss and a following lever portion
a second leg portion coupled to the following lever portion,
wherein the second blade is coupled to the second leg portion such that when the second boss moves in the longitudinal direction with respect to the activator, the second yoke pivots about the second fulcrum causing the second blade to rotate,
a fourth fulcrum coupled to the second blade holder,
a fourth yoke pivotedly coupled to the fourth fulcrum having a driving lever portion coupled to the boss and a follower lever portion,
a fourth leg portion coupled to the following lever portion,
wherein the fourth blade is coupled to the fourth leg portion such that when the second boss moves in the longitudinal direction with respect to the activator, the fourth yoke pivots about the fourth fulcrum causing the fourth blade to rotate.

2. The surgical retractor of claim 1, wherein the first blade is removeably coupled to the first leg portion, the second blade is removeably coupled to the second leg portion, the third blade is removeably coupled to the third leg portion, and the fourth blade is removeably coupled to the fourth leg portion.

3. The surgical retractor of claim 1, wherein the first leg portion has at least one protrusion to engage one of a plurality of corresponding teeth on a surface of the first blade such that the first blade is longitudinally adjustable with respect to the first leg portion.

4. The surgical retractor of claim 1, wherein the first activator is a screw having external threads which rotatingly engage interior threads of a bore defined in the first boss to move the boss in the longitudinal direction with respect to the first activator.

5. The surgical retractor of claim 1, wherein the first boss has at least one wing having a first slanted engagement surface to engage a second slanted engagement surface of the first yoke.

6. The surgical retractor of claim 1, wherein the first fulcrum is a pin coupled to the first yoke.

7. The surgical retractor of claim 1, wherein the length adjustment mechanism comprises a bar, a first rack coupled to the bar, a second rack coupled to the bar, and a gear coupled to the bar, the first rack and the second rack; wherein the gear is configured to move the first rack relative to the second rack to move the first blade holder relative to the second blade holder.

8. The surgical retractor of claim 7, wherein the length adjustment mechanism includes a stop coupled to the gear and removably coupled to the first rack, and where movement of the first blade holder relative to the second blade holder is inhibited until the stop is decoupled from the first rack.

9. The surgical retractor of claim 1, wherein at least one of the blades include a longitudinal slot and a light mat position within the slot.

10. The surgical retractor of claim 1, wherein at least one blade is made from a translucent material and includes light receiving couplers formed in a proximal portion of the blade and light directing notches cut in a distal portion of the blade.

11. The surgical retractor of claim 1, further comprising
a first recess positioned within the first blade holder,
a second recess positioned within the second blade holder,
a side blade having a fixed portion coupled to the first recess and the second recess and a rotating portion rotatingly coupled to the fixed portion.

12. A method of using a surgical retractor comprising:
slidingly separating a first blade holder from a second blade holder, wherein the first blade holder includes a first blade angle adjustment mechanism and the second blade holder includes a second blade angle adjustment mechanism,
rotating a first blade with respect to the first blade holder, wherein the rotating comprises:
activating a first activator to move a first boss longitudinally with respect to the first activator,
pushing against a driving lever of a first yoke with the first boss to cause the first yoke to pivot about a first fulcrum,
moving the first blade with a follower lever of the first yoke as the first yoke pivots about the first fulcrum such that the angle between the first blade and the first blade holder is adjusted, and
rotating a second blade with respect to the first blade holder, wherein the rotating comprises:
activating the first activator to move the first boss longitudinally with respect to the first activator,
pushing against a driving lever of a second yoke with the first boss to cause the second yoke to pivot about a second fulcrum,
moving the second blade with a follower lever of the second yoke as the second yoke pivots about the second fulcrum such that the angle between the second blade and the first blade holder is adjusted.

13. The method of claim 12, further comprising:
rotating a third blade with respect to the second blade holder, wherein the rotating comprises:
activating a second activator to move a second boss longitudinally with respect to the second activator,
pushing against a driving lever of a third yoke with the second boss to cause the third yoke to pivot about a third fulcrum,
moving the third blade with a follower lever of the third yoke as the third yoke pivots about the third fulcrum such that the angle between the third blade and the second blade holder is adjusted, and
rotating a fourth blade with respect to the second blade holder, wherein the rotating comprises:
activating the second activator to move the second boss longitudinally with respect to the second activator,
pushing against a driving lever of a fourth yoke with the second boss to cause the fourth yoke to pivot about a fourth fulcrum,
moving the fourth blade with a follower lever of the fourth yoke as the fourth yoke pivots about the fourth fulcrum such that the angle between the fourth blade and the second blade holder is adjusted.

14. The method of claim 12, further comprising coupling the first blade to a blade support which is coupled to the following lever of the first yoke.

15. The method of claim 12, wherein the activating the first activator further comprises turning a member having external threads engaged with internal threads of the first boss, such that the first boss travels longitudinally with respect to the first activator.

16. The method of claim 12, wherein the slidingly separating comprises disengaging a round gear from a stop such that the gear engages a first plurality of teeth coupled to the first blade holder and a second plurality of teeth coupled to the second blade holder such that first blade holder moves with respect to the second blade holder.

17. The method of claim 13, further comprising illuminating an area between the first blade and the third blade with a light mat coupled to at least one of the first blade or third blade.

18. The method of claim 13, further comprising illuminating an area between the first blade and the third blade with a translucent blade having one or more slits to direct light.

19. A surgical kit, comprising:
a first retractor comprising:
a first blade holder with at least one blade support member,
a second blade holder with at least one blade support member,
a first length adjustment mechanism slidingly coupled to the first blade holder and the second blade holder, the first length adjustment mechanism configured to move the first blade holder relative to the second blade holder;
a first pair of arms with a first predetermined length, wherein the first pair of arms are configured to couple the length adjustment mechanism to the first blade holder and the second blade holder;
a second retractor comprising:
a first blade holder with at least one blade support member,
a second blade holder with at least one blade support member,
a second length adjustment mechanism slidingly coupled to the first blade holder and the second blade holder of the second retractor, the second length adjustment mechanism configured to move the first blade holder relative to the second blade holder of the second retractor;
a second pair of arms with a second predetermined length, wherein the second pair of arms are configured to couple the second length adjustment mechanism to the first blade holder and the second blade holder of the second retractor, and a plurality of sets of blades configured to couple to the blade support members, wherein the blades in each set have the same length and the blades of differing sets have different blade lengths;

at least one driver configured to activate moving components of the length adjustment mechanisms and the blade holders, at least a pair of shims, and a blade adjustor configured to couple to the blades.

20. The surgical kit of claim 19, further comprising a first blade angle adjustment mechanism coupled to the first blade holder and adapted to couple to at least one blade in the plurality of sets of blades, the first blade angle adjustment mechanism including:

a first activator, a first boss coupled to the first activator such that when the first activator is activated, the first boss moves in a longitudinal direction with respect to the first activator, a first fulcrum coupled to the first blade holder, a first yoke pivotedly coupled to the first fulcrum having a driving lever portion coupled to the boss and a follower lever portion, a first leg portion coupled to the follower lever portion, wherein the at least one blade is coupled to the first leg portion such that when the first boss moves in the longitudinal direction with respect to the activator, the first yoke pivots about the first fulcrum causing the at least one blade to rotate.

* * * * *